United States Patent [19]

Bayless

[11] Patent Number: 5,372,742

[45] Date of Patent: Dec. 13, 1994

[54] NAIL POLISH REMOVER

[75] Inventor: Ronnie E. Bayless, Plant City, Fla.

[73] Assignee: Dotolo Research Corporation, Largo, Fla.

[21] Appl. No.: 7,565

[22] Filed: Jan. 22, 1993

[51] Int. Cl.$^5$ .............. A61K 7/047; C11D 7/26; C11D 7/50

[52] U.S. Cl. .................. 252/170; 134/38; 252/162; 252/171; 252/174.21; 252/364; 252/DIG. 8; 424/61; 424/401

[58] Field of Search ........... 252/162, 170, 171, 174.21, 252/364, DIG. 8; 424/61, 401; 134/38

[56] References Cited

U.S. PATENT DOCUMENTS

| | | | |
|---|---|---|---|
| 3,686,701 | 8/1972 | Charle et al. | 252/364 |
| 3,870,536 | 3/1975 | Blanco et al. | 106/146 |
| 3,882,248 | 5/1975 | Igimi et al. | 424/356 |
| 4,620,937 | 11/1986 | Dellutri | 252/143 |
| 4,710,497 | 12/1987 | Heller et al. | 514/221 |
| 5,011,621 | 4/1991 | Sullivan | 252/162 |
| 5,063,057 | 11/1991 | Spellman et al. | 424/401 |
| 5,082,660 | 1/1992 | Ounanian et al. | 424/63 |
| 5,098,591 | 3/1992 | Stevens | 252/162 |
| 5,110,584 | 5/1992 | Medri et al. | 424/61 |
| 5,215,675 | 6/1993 | Wilkins et al. | 252/542 |

FOREIGN PATENT DOCUMENTS

| | | | |
|---|---|---|---|
| 3-37299 | 2/1991 | Japan | 252/171 |
| 3-41170 | 2/1991 | Japan | 252/170 |
| 4-323299 | 11/1992 | Japan . | |

*Primary Examiner*—Linda Skaling
*Attorney, Agent, or Firm*—Marshall & Melhorn

[57] ABSTRACT

A liquid, non-aqueous cleaner composition that is well suited for removing finger nail polish, the composition comprising d-limonene, ethyl lactate, cetyl acetate, and optionally, propylene glycol methyl ether acetate.

10 Claims, No Drawings

NAIL POLISH REMOVER

FIELD OF THE INVENTION

The present invention relates to a coating removal and all-purpose cleaning composition and, more particularly, to a fingernail polish remover.

BACKGROUND OF THE INVENTION

Conventional nail polish remover compositions generally include acetone, ethyl acetate and alcohol. The use of acetone, ethyl acetate and alcohol is disadvantageous in that it gives off a disagreeable odor, is irritating to the eyes and skin, and is drying to the nails and cuticles. Acetone, ethyl acetate and alcohol are flammable and combustible and can be harmful to the user.

OBJECTS OF THE INVENTION

It is an object of the present invention to provide an easy-to-make, easy-to-use very efficient nail polish remover composition and methods of using the compositions.

It is a further object of the present invention to provide a very effective, non-toxic, non-methylene chloride, acetone, ethyl acetate or alcohol containing nail polish remover comprising d-limonene, ethyl lactate, and cetyl acetate, or a mixture of cetyl acetate and acetylated lanolin alcohol.

Still another object of the present invention to provide a non-aqueous liquid cleaning composition especially adapted for removing finger nail polish, the composition comprising the following ingredients in approximate percent by weight:

| Ingredients | % by weight |
| --- | --- |
| 1. d-limonene | 20–70 |
| 2. ethyl lactate | 20–70 |
| 3. cetyl acetate or a mixture of cetyl | 1–15 |

These and other objects will be apparent from the specification and claims that follow.

SUMMARY OF THE INVENTION

The present invention provides a non-aqueous composition comprising the following ingredients:
1. d-limonene;
2. ethyl lactate;
3. cetyl acetate or a mixture of cetyl acetate and acetylated lanolin alcohol; and
4. optionally, propylene glycol methyl ether acetate.

The present invention provides an effective, non-toxic, non-aqueous liquid finger nail cleaner composition comprising the following ingredients in the general and preferred ranges set forth in approximate percent by weight:

| Ingredients | % by weight | | |
| --- | --- | --- | --- |
|  | General | Preferred | Ideal |
| 1. d-limonene | 20–70 | 30–60 | 45 |
| 2. ethyl lactate | 20–75 | 25–55 | 50 |
| 3. cetyl acetate | 9–17 | 12–15 | 5 |

Optionally, propylene glycol methyl ether can be used as well as a surfactant. These formulations are as follows in approximate % by weight:

| Ingredient | Optimal | General |
| --- | --- | --- |
| 1. d-limonene | 27 | 15–50 |
| 2. ethyl lactate | 35 | 10–50 |
| 3. propylene glycol methyl ether acetate | 35 | 10–50 |
| 4. Acetulan | 2 | 1–50 |
| 5. surfactant (ethoxylated undecyl alcohol) | 1 | 0.1–5 |

DETAILS OF THE INVENTION

The compositions of the present invention, while preferably used as a nail polish remover, on silk line, and fiberglass wraps. The compositions are useful as all-purpose cleaners and, in particular, hard surface cleaners, blanket washes for us in the printing industry, cleaners for brake linings, silk screens, copier belts, all kinds of metering devices including coin collecting machines, and the cleaning of all types of spraying equipment when used for painting, applying glues, inks, greases, oils, etc.

The easy to use, easy to make cleaning composition is made by mixing generally the three liquid ingredients (d-limonene, ethyl lactate and Acetulan) to form a homogenized stable cleaning mixture having enhanced detergent and stripping powers. When ethyl lactate is used, the speed of the cleaning action increases. This combination of Acetulan, d-limonene and ethyl lactate is necessary for the removal of some of the new hard finishes of certain nail polishes, especially when the polishes are on wrapped nails. The d-limonene component is a solvent or diluent that assists in penetrating and stripping or removing of the coating (such as finger nail polish) to be removed.

The d-limonene helps to loosen or dissolve grease, fat or organic materials, and is described as an ingredient in a cleaner in U.S. Pat. Nos. 4,790,951 and 5,031,648.

When N-methyl pyrrolidone (NMP) was used as a solvent in the composition, the results were not satisfactory especially when compared to the remover containing the above three ingredients. U.S. Pat. No. 4,605,670 discloses a percutaneous (drug) absorption composition including NMP and other ingredients such as alcohols or esters including cetyl acetate. U.S. Pat. No. 5,011,621 is directed to a paint stripper composition and discloses the use of NMP, an oil, and a plurality of cosolvents including terpenes. U.S. Pat. No. 5,098,591 (Stevens) discloses a paint stripper composition that includes NMP.

The cetyl acetate is a desensitizer that enhances the compatibility, efficiency, miscibility, and stability of the liquid non-aqeous d-limonene/NMP combination. As indicated, cetyl acetate should be at least about 1 percent by weight of the composition with the best results being obtained with about 2 to 6 percent by weight. Acetulan, a mixture of cetyl acetate and acetylated lanolin alcohol, can be used in place of all or part of the cetyl acetate.

As indicated, relatively large amounts of ethyl lactate can be used, say, about 10 to 20 up to 50 or 70% by weight. Preferably about 30 to 55 weight percent is used to obtain fast drying. Ethyl lactate is a solvent that is compatible with d-limonene, cetyl acetate, Acetulan (mixture of cetyl acetate and acetylated lanolin alcohol), and the optional ingredient (propylene glycol methyl ether acetate). Ethyl lactate enhances the compatibility, efficiency, miscibility, and the stability of the liquid, the speed of drying the non-aqueous d'limonene/acetulan combination and enhances the removal time for the more difficult hard nail polish surfaces. Best results are obtained with about 40–50% by weight. As indicated, the total amount of d-limonene in the composition is preferably at least 20 or 30 percent by weight and more preferably at least about 27 or 45 percent by weight. In some cases, methyl lactate can be used with the ethyl lactate, the methyl lactate being generally about 3 to 5 weight percent up to 50 to 55 weight percent of the combination of ethyl lactate and methyl lactate.

The cleaner composition has an outstanding balance of properties including easy removal of coatings (finger nail polish) on hard surfaces, being non-irritating, having a pleasant order, being quick drying, having miscible ingredients, and leaving the cleaned surfaces free of surface fiber.

The present invention provides the following composition in which the ingredients are present in percent by weight:

| Ingredients | % by weight |
| --- | --- |
| 1. d-limonene | 30–60 |
| 2. ethyl lactate | 25–45 |
| 3. cetyl acetate | 2–7. |

Also provided is a composition in which the following ingredients are present in approximate percent by weight:

| Ingredients | % by weight |
| --- | --- |
| 1. d-limonene | 30–60 |
| 2. ethyl lactate | 10–50 |
| 3. cetyl acetate | 1–5 |
| 4. propylene glycol methyl ether acetate | 10–50. |

Also provided is a composition comprising about 40% by weight of d-limonene, about 45% by weight of ethyl lactate, about 5% by weight of cetyl acetate and acetylated lanolin alcohol, and propylene glycol methyl ether acetate in an amount of at least about 10% by weight.

What is claimed is:

1. A non-aqueous cleaning composition consisting essentially of the following ingredients in approximate percent by weight:

| Ingredients | % by weight |
| --- | --- |
| 1. d-limonene | 20–70 |
| 2. ethy lactate | 20–70 |
| 3. cetyl acetate or a mixture of cetyl acetate and acetylated lanolin alcohol | 1–15 |

2. A composition as defined in claim 1 in which the following ingredients are present in approximate percent by weight:

| Ingredients | % by weight |
| --- | --- |
| 1. d-limonene | 30–60 |
| 2. ethyl lactate | 25–45 |
| 3. cetyl acetate | 2–7 |

3. A non-aqueous cleaning composition consisting essentially of the following ingredients in approximate percent by weight:

| Ingredients | % by weight |
| --- | --- |
| 1. d-limonene | 30–60 |
| 2. ethyl lactate | 10–50 |
| 3. cetyl acetate | 1–5 |
| 4. propylene glycol methyl ether acetate | 10–50 |

4. A composition as defined in claim 1 consisting essentially of about 45 weight percent d-limonene, 50 weight percent ethyl lactate, and 5 weight percent cetyl acetate or a mixture of cetyl acetate and acetylated lanolin alcohol.

5. A composition as defined in claim 1 in which there is about 0.1 to 5 weight percent of ethoxylated undecyl alcohol.

6. A composition as defined in claim 1 in which a portion of the ethyl lactate is substituted for by methyl lactate in which methyl lactate is about 3 to 55 weight percent of the mixture of methyl lactate and ethyl lactate.

7. A composition as defined in claim 3 consisting essentially of about 40% by weight of d-limonene, about 45% by weight of ethyl lactate, about 5% by weight of cetyl acetate and acetylated lanolin alcohol, and propylene glycol methyl ether acetate in an amount of at least about 10% by weight.

8. A liquid non-aqueous cleaner composition as defined in claim 1, the composition being adapted to remove finger nail polish, the composition consisting essentially of d-limonene, about 2 to 7 weight percent of a mixture of cetyl acetate and acetylated lanolin alcohol, ethyl lactate and about 0.1 to 5 weight percent of ethoxylated undecyl alcohol.

9. A non-aqueous cleaning composition consisting of the following ingredients in approximate percent by weight:

| Ingredients | % by weight |
| --- | --- |
| 1. d-limonene | 20–70 |
| 2. ethy lactate | 20–70 |
| 3. cetyl acetate or a mixture of cetyl acetate and acetylated lanolin alcohol | 1–15 |

10. A method of removing a coating from a fingernail comprising:
a) applying the cleaning composition defined in claim 1 to the coating on the nail;
b) allowing the coated nail and composition to remain in contact for a time sufficient to loosen the coating from the nail, and
c) separating the coating and the composition from the nail.

* * * * *